United States Patent
Bienhaus et al.

[11] Patent Number: 5,837,144
[45] Date of Patent: Nov. 17, 1998

[54] METHOD OF MAGNETICALLY SEPARATING LIQUID COMPONENTS

[75] Inventors: Gerhard Bienhaus, Wielenbach; Burkhard Stolz, Huglfing; Ulrich Schubert, Starnberg, all of Germany

[73] Assignee: Boehringer Mannheim GmbH, Mannheim, Germany

[21] Appl. No.: 490,986

[22] Filed: Jun. 15, 1995

[30] Foreign Application Priority Data

Jun. 16, 1994 [DE] Germany .......................... 44 21 058.2

[51] Int. Cl.[6] .................................................. B01D 35/06
[52] U.S. Cl. .......................................... 210/695; 436/526
[58] Field of Search .................................. 210/222, 695; 436/526; 209/214, 223.2; 294/65.5

[56] References Cited

U.S. PATENT DOCUMENTS

| | | | |
|---|---|---|---|
| 3,985,649 | 10/1976 | Eddelman | 210/695 |
| 4,649,116 | 3/1987 | Daty et al. | 210/222 |
| 5,043,063 | 8/1991 | Latimer | 210/222 |
| 5,647,994 | 7/1997 | Tuunanen et al. | 210/222 |

FOREIGN PATENT DOCUMENTS

| | | |
|---|---|---|
| 0 136 126 | 9/1984 | European Pat. Off. . |
| 0 265 244 | 10/1987 | European Pat. Off. . |
| 0 339 980 | 4/1989 | European Pat. Off. . |
| 0 589 636 | 9/1993 | European Pat. Off. . |
| WO 86/06493 | 11/1986 | WIPO ..................................... 436/526 |
| WO 87/05536 | 9/1987 | WIPO ..................................... 294/65.5 |
| WO 94/18565 | 8/1994 | WIPO ..................................... 436/526 |

OTHER PUBLICATIONS

Hersh et al, Clinica Chimica Act., "Magnetic Solid–Phase Radioimmunoassy", 63 (1975) 69–72.
Biotechnology and Bioengineering, "The Properties of Magnetic Supports in Relation to Immobilized Enzyme Reactors", vol. XV, (1973).
International Publication No. WO 92/16844 published Oct. 1, 1992.
International Publication No. WO 93/25912 published Dec. 23., 1993.
International Publication No. WO 92/04961 published Apr. 2, 1992.

Primary Examiner—Matthew O. Savage
Attorney, Agent, or Firm—Nikaido Marmelstein Murray & Oram LLP

[57] ABSTRACT

Method of separating a component of a liquid from other components by immobilizing the component to suspended magnetic particles in a vessel, immersing a magnetic device into the vessel while the device is separated from the liquid by means of a protective sleeve made of a non-magnetic material. Then the non-immobilized components are removed. The invention also addresses a device suitable for implementing this method. With said method and device, resuspension is achieved in a simple and efficient manner.

8 Claims, 3 Drawing Sheets

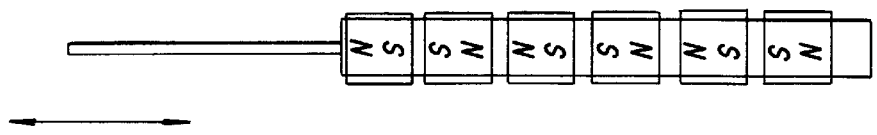
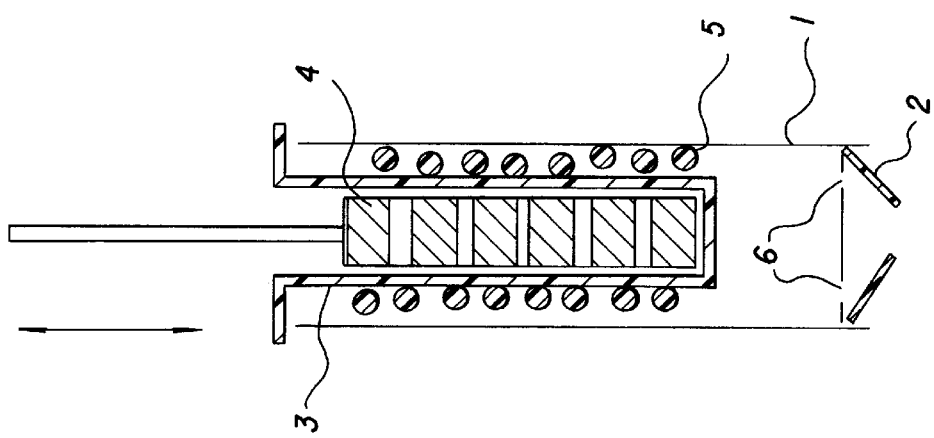

METHOD OF MAGNETICALLY SEPARATING LIQUID COMPONENTS

Subject matter of the invention is a method of separating a component of a liquid from another component of this liquid and a device for the implementation of said method.

When components of a liquid, especially constituents of body fluids, are analyzed, a frequently recurring problem is that the liquid contains only minor amounts of this component and also several very similar components. For this reason, the actual detection of the component is preceded by a step for amplifying or purifying the component to be detected. A commonly used way is the selected immobilization of the component to a solid phase while the liquid which contains similar components is subsequently separated. The immobilized components are then detected either directly at the solid phase or after transfer into another liquid. Possible solid phases are absorbent fleeces, container walls, or particle-like phases.

Recently, one has come to appreciate magnetic or magnetizable parts as solid phases as their ability to become suspended allows for a sufficiently rapid immobilization of the components to their surface. On the other hand, they can also be rapidly separated from the surrounding liquid by applying a magnetic field thereto. EP-A-0 589 636 describes an example for a method of magnetically separating magnetic particles. In this method, the vessel containing the particles is introduced into a device which has one or several bar magnets located in neighbourhood to the lower part of the vessel to collect the magnetic particles in the lower part of the inner wall of the vessel.

WO 92/04961 describes a method where the magnetic forces which act from the outside are enhanced in that a magnetizable wire is immersed. The magnetic particles are retained at the wires. Subsequently, the wires can be removed from the vessel, washed, and the amount of components immobilized on the wire can be determined.

EP-A-0 339 980 also describes a method of separating magnetic particles from surrounding liquids, wherein magnets which are attached to the outside of the pipette are used to immobilize magnetic particles to a wire located inside the pipette. After washing the immobilized particles, they are resuspended through vibration of the wires.

EP-A-0 265 244 describes a method for the capture of substances to be detected at magnetic particles, and the removal of the magnetic particles from the liquid containing the substances to be tested.

Cell separation can also be accomplished with the aid of devices in the form of filters with integrated steel wool to enhance the effect of the magnet or sharp-edged ferrites (DE-A42 44 369).

These methods are little suitable for automation as either the tube has to be transported (WO 93/25912) or the magnets have to be moved towards the reaction vessels. WO 92/16844 describes a possibility of automating this process, which, however, includes a significant risk of contamination while resuspension is still insufficient. In this case, the magnets are also located outside the reaction vessels.

A drawback of methods described to date is that they require a resuspension procedure which is complicated and frequently little efficient. The wires, once they have been immersed into the sample liquid, cannot be easily reused.

It was, hence, an object of the present invention to provide a process where the magnetic particles are separated in an efficient manner and where the parts of the devices necessary for the immobilization are protected against contamination.

Subject matter of the invention is, hence, a method of separating a component of a liquid from other components by immobilizing said first component to magnetically suspended particles in a vessel, immersing a permanently magnetic device into the vessel, whereby the device has a protective sleeve to separate it from the liquid, and by removing non-immobilized components. Another subject matter of the invention is a method of detecting the component and a device for implementing said method.

Liquids as understood in the invention are in particular those used in clinical analysis. They include especially body fluids, such as blood, serum, plasma, lymphatic fluid, stool, sputum, or urine as well as liquids derived therefrom. Derived liquids are those that have been prepared by adding reagents or removing individual components. Components of these liquids are especially chemical substances of analytical importance such as immunologically active substances, e.g. antibodies, antigens, haptens, but also nucleic acids, e.g. from the cells of the corresponding body, and organisms that may have invaded this body such as viruses or bacteria, and cells, e.g. cells of the body's immunological system such as lymphocytes. All these components are present in the liquids in a mixture with other components from which they often differ only slightly.

The device of the invention is well suited for sample preparation for nucleic acid analysis.

In the method of the invention, the interaction of the component to be separated with a reaction partner to bind to a magnetic particle is utilized in a known manner. Such interactions depend upon the component. Particularly suitable interactions are immunological reactions between antibodies and antigens and the tendency of nucleic acids to hybridize to essentially complementary nucleic acids. Automated reactions using magnetic particles are known in the most different variants, including U.S. Pat. No. 4,233,169, WO 83/03920, U.S. Pat. No. 3,970,518, or U.S. Pat. No. 4,672,040. The conditions mentioned therein to immobilize a component from the liquid can also be applied to the present invention.

A vessel is understood to be a container holding the liquid as well as the components contained therein. This can be a vessel which is closed at its bottom, e.g. a tube, a cuvette or an Eppendorf tube. In accordance with the invention, it may also be a vessel which can be opened at its bottom. These vessels are made of a non-magnetic and non-magnetizable material such as glass or plastic, preferably polystyrene, polyethylene, polypropylene, polycarbonate, or polyurethane. In a preferred manner, this vessel has a volume between 50 $\mu$l and 10 ml, particularly preferred between 200 $\mu$l and 2 ml. The preferred form of the vessels is an essentially cylindrical one, with the length exceeding the diameter.

Magnetic particles are in particular microparticles which are attracted by means of a magnetic field. They can, hence, themselves be magnetized. Materials with a yery small remanence are preferred. The material of the particles may be a compound material, such as a matrix containing magnetically attractable parts. The magnetically attractable material can, for example, be iron, iron oxides, nickel, cobalt, or chromium oxide. The matrix can be made of various different materials, for example, organic or inorganic polymers. The magnetic particles are coated with a binding partner for the component to be separated. Both the manufacturing of magnetic particles as well as their coating with immunologically active compounds or their covalent linking to nucleic acids are known from prior art, for example, from U.S. Pat. No. 4,297,337 or DE-A-30 14 036.

Such particles are also commercially available, for example by Dynal or Rhone-Poulenc. The latter particles are preferred for use in the method of the invention as they form relatively stable suspensions.

In a first step of the method of the invention, the liquid containing the component is brought into contact with the magnetic particles. During incubation, the particles are preferably present in a suspension. As a consequence of the interaction of the surface of the particles with a component to be separated, the component is immobilized on the particles. This reaction step is carried out in one of the above-mentioned vessels.

Once a sufficient amount of component to be separated has been immobilized on the particles, the invention proposes to immerse a magnetic device into the vessel. At least a part of the device should extend below the liquid level. In accordance with the invention, the device is separated from the liquid by means of a protective sleeve made of a non-magnetic material. This protective sleeve can be made of plastic, for example. The device and the protective sleeve can principally be immersed in two different ways. In a first embodiment, first the protective sleeve is immersed into the liquid in a vessel so that a part of the hollow body formed by the protective sleeve extends below the liquid level. In this case, the protective sleeve can have a form of a lid for the vessel which may be manually or automatically placed onto the vessel from the top. In a subsequent step, the magnetic device is introduced in the hollow body of the lid from the top so that at least a part of the device comes to rest below the liquid level.

The device can principally be a permanently magnetic or a magnetizable device, e.g. an electromagnetic device. Provided the device is a permanently magnetic device, the suspended particles migrate to the interface between liquid and protected sleeve after immersion of the device and precipitate there. In case the device is magnetizable, for example an electromagnet, this precipitation occurs after applying a magnetic field to the device.

If necessary or desired, the particles can be removed from the protective sleeve by applying a magnetic field outside the vessel and be resuspended, followed by another precipitation at the surface of the protective sleeve. In another step of the process of the invention, the liquid which contains non-immobilized components is removed from the particles adhering to the surface of the protective sleeve. This can be done in a conventional manner, for example, by absorbing or draining the liquid (if the vessel is pipette-like); it is, however, also possible to remove the device together with the protective sleeve and the immobilized particles from the liquid. Absorbing and draining are preferred.

In many cases, a rest of the liquid together with other components will still adhere to the immobilized particles. If this interferes with the further treatment, the particles can be freed from other components by means of washing. To accomplish this, the device with the protective sleeve and the particles thereon is immersed into a washing liquid, the immobilization of the particles is stopped by eliminating the magnetization or removing the magnetic device, or a magnet located outside the vessel is used to attract the particles. The particles are then again immobilized to the protective sleeve by reintroducing the magnetic device or applying the magnetic field. As described above for the sample liquid, the washing liquid can then also be removed.

In one embodiment, the device of the invention can also be used to transfer magnetic particles from a reaction mixture of the first vessel into another vessel. This cannot be easily done in other known methods.

The method of the invention is distinguished by the fact that resuspension of the magnetic particles is particularly efficient. Experience has shown that when the magnetic device is slowly withdrawn from the protective sleeve as long as the latter is still immersed in the liquid, resuspension is much better as compared removing the device with the aid of a magnet located outside the vessel. The velocity at which the magnetic device is withdrawn from the protective sleeve preferably ranges between 0.1 mm/sec and 50 mm/sec, particularly preferred between 0.5 mm/sec and 10 mm/sec. These velocities can be implemented in a particularly simple manner with the aid of a lifting device located at an XYZ arm of an automated pipetting arm. Further additional modules are then not required.

The so purified components are now ready for further treatment, for example a detection reaction. The expert knows several methods for this purpose. To accomplish this, the components can, for example, be released from the magnetic particles (in case of nucleic acids, by means of dehybridization), and then be separated from the particles.

Subject matter of the invention is, hence, also a method of detecting a component of a liquid by separating this component in accordance with the invention and then detecting said component.

Another subject matter of the invention is a device for separating a component of a liquid from other components, comprising one or several vessels for receiving the liquid, one or several protective sleeves extending into the vessels, a magnetic device extending into the protective sleeve and the vessel, and a lifting device for introducing the protective sleeve and the magnetic device into the vessel and retracting it again. The vessels and the protective sleeves can be stored in magazines. As soon as the particles are to be separated, a protective sleeve is taken from the magazine and introduced into the vessel, either together with or separated from the magnetic device with the aid of this lifting device. The lifting device can be attached to an XYZ arm of a pipetting robot, e.g. one manufactured by Tecan.

In a preferred manner, the magnetic device of the invention has a sandwich-like arrangement of small bar magnets. The poles are arranged alternatingly in lifing direction (FIG. 1). Principally, it is also possible to have an arrangement of individual bar magnets as described in EP-A-0 136 126. An arrangement outside the vessel is, however, not possible. In a preferred embodiment (FIG. 2), the bar magnets are arranged vertically such that identical poles face each other. In a particularly preferred manner, the individual bar magnets are separated by small steel plates. In an embodiment with electromagnets, these magnets are individually and horizontally disposed. The poles have a star-like arrangement in different planes. This ensures a uniform precipitation of the magnetic particles. In this case, it is preferred to have a lifting device which can be additionally rotated.

In the device of the invention, a second or yet another magnet may be provided in addition to the magnetic device and be located outside the vessel. They can be advantageously used for resuspending the magnetic particles.

A particularly advantageous embodiment is when form and contents of vessel and protective sleeve as well as the volume of liquid optimally match. In a particularly preferred manner, the form of the protective sleeve is selected such that its outer surface is always spaced apart from the inner surface of the vessel by approximately the same distance. An example of such an arrangement includes two cylindrical forms where one is located inside the other. The space formed by the two walls can be filled by the liquid. This means prior to entering the protective sleeve into the vessel, the amount of liquid filled into the vessel must not exceed this volume. When the protective sleeve is introduced into the vessel, the liquid is then pressed between the cylindrical walls.

In this embodiment, where the space formed between the protective sleeve and the inner surface of the vessel is filled with sample liquid by introducing the protective sleeve, the use of electromagnetic devices is particularly preferred. By distributing the liquid in a relatively thin layer around the magnetic device, the field strength which can be obtained with electromagnets is sufficient. In arrangements described in prior art, this has not been accomplished.

Further, the protective sleeve preferably contains means to remove the protective sleeve from the vessel. These are preferably parts included in the inner section of the protective sleeve where the lifing device engages.

The process of the invention has the advantage that it is easy to automate. Moreover, it is also advantageous that resuspension can be achieved simply and effectively. Surprisingly, the attracted particles can be resuspended in a particularly efficient manner through the lifting and rotating movement of the magnet. This is accomplished in particular when the magnetic device moves slowly up and down. Moreover, the use of a protective sleeve ensures that the risk of contamination is largely reduced. This risk is particularly critical because of the aerosols involved and during cell isolation followed by amplification of the nucleic acids. For this purpose, the protective sleeve may be designed as a disposable element and may fulfill a dual function serving also as a lid for the vessel. Because of the layered structure of small bar magnets, the magnetic particles will precipitate over a broader area thus facilitating washing and resuspension.

FIG. 1 shows an embodiment of the invention including a vessel, protective sleeve, and magnetic device.

FIG. 2 shows a magnet device for use with the invention.

Figure 4:
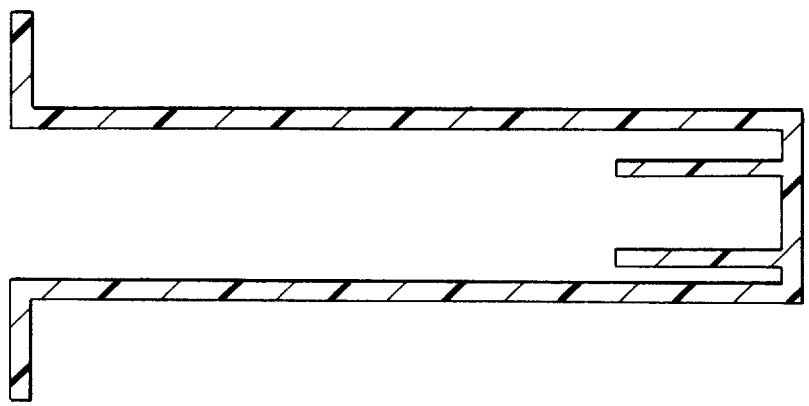
FIG. 4 shows a protective sleeve for use with the invention.

FIG. 1 shows a plastic vessel (1) with an open rubber sealing lip (2) into which the protective sleeve (3) extends. Said protective sleeve contains a magnetic device (4) consisting of six bar magnets, for example. Plastic vessels of this type can be manufactured in injection molding processes. They have an essentially cylindrical base and a bottom with at least two bores. The rubber sealing lip preferably has the form of a rubber disk with an opening that does not coincide with the bores (6) of the bottom of the plastic vessel. When a low pressure is applied to the bottom of the vessel, the rubber sealing lip is retracted from the bottom and the liquid can exit through the bores in the bottom. Magnetic particles (5) are relatively uniformly distributed at the outer wall of the protective sleeve.

FIG. 2 is a magnetic device where six bar magnets are arranged such that their poles alternate.

Figure 3:
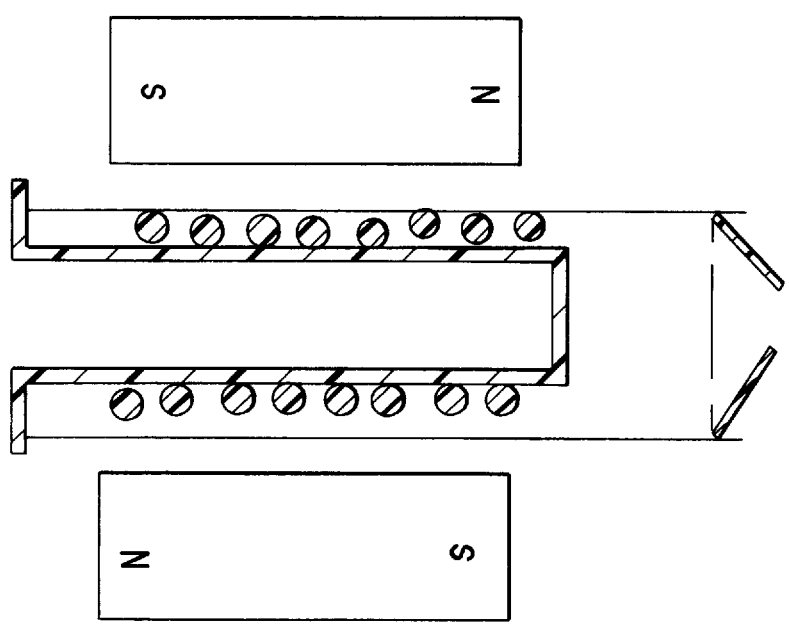
FIG. 3 shows an embodiment of the invention including a magnet device located outside the vessel.

FIG. 3 shows a vessel with a protective sleeve and magnetic particles where additional magnets are attached to the outside of the wall of the vessel.

FIG. 4 shows a cross section taken through the protective sleeve where means for removing the protective sleeve from the vessel are located in the interior.

Figure 5:
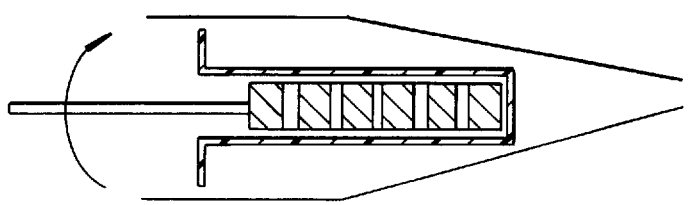
FIG. 5 shows a vessel including a pipette tip for use with the invention.

FIG. 5 shows a device in accordance with the invention where the vessel has the form of a pipette tip.

Figure 6:
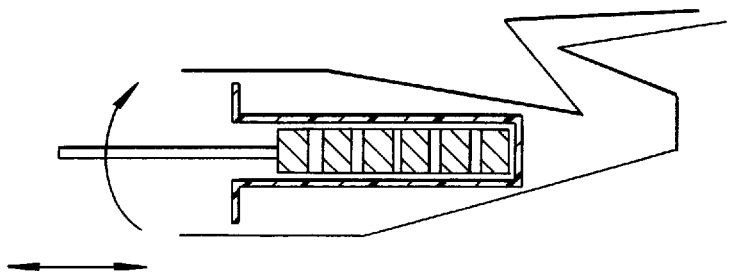
FIG. 6 shows a vessel employing a syphon for use with the invention.

FIG. 6 shows an embodiment derived therefrom where a syphon is used to prevent the loss of magnetic particles during transfer.

The protective sleeve and the magnetic device can be introduced together or sequentially into the vessel containing the magnetic particles and immobilized components attached thereto. The protective sleeve and the magnetic device are handled by an appropriate lifting means, with various types of lifting means being well known to those in the art. For instance, the projections at the bottom of the protective sleeve of FIG. 4 can be engaged by a suitable robotic arm, such as, that disclosed in U.S. Pat. No. 4,927,545, the disclosure of which is hereby incorporated by reference for such teaching.

The prior art documents identified hereinabove are hereby incorporated by reference for the indicated teachings therein.

We claim:

1. A method of separating a first component of a liquid from other components in the liquid utilizing magnetic particles, comprising the steps of:

(a) providing a vessel;

(b) adding the liquid and a quantity of magnetic particles therein to form a suspension of the magnetic particles and the liquid within said vessel;

(c) immobilizing the first component on the suspended magnetic particles in the vessel;

(d) immersing a magnetic device into the suspension contained in the vessel, while separating the device from the suspension by means of a protective sleeve which is made of a non-magnetic material, to apply a magnetic field to the suspension to adhere the magnetic particles having the first component immobilized thereon to the protective sleeve, and thereafter (e) separating the other components from the immobilized first component by removing the liquid containing the other components from the vessel while maintaining the protective sleeve with the magnetic particles having the first component immobilized thereon adhering to the protective sleeve within the vessel.

2. Method of claim 1, wherein in step (e) the liquid containing the non-immobilized components is removed from the vessel through bores in a bottom wall of the vessel.

3. Method of claim 1, further comprising the step of withdrawing the protective sleeve from the vessel with the magnetic particles adhered to the protective sleeve and with said first component immobilized on the magnetic particles after step (e).

4. Method of claim 2, wherein the magnetic device includes a longitudinal axis and a plurality of permanent magnets or electromagnets stacked along said axis, wherein said magnets define magnetic poles which alternate in polarity in a direction parallel to said axis.

5. Method of claim 1, wherein the first component is cells.

6. Method of claim 1, wherein the first component is nucleic acids.

7. Method of claim 1, further comprising the step of adding a wash liquid to the vessel after step (e), and re-suspending the magnetic particles with the first component immobilized thereon in said wash liquid to wash said magnetic particles and said first component.

8. Method of claim 7, wherein said step of re-suspending includes the step of rotating and/or lifting the magnetic device with respect to said vessel.

* * * * *